United States Patent [19]

Schubert

[11] 4,167,814
[45] Sep. 18, 1979

[54] MOUTH PROP AND ORAL EVACUATION DEVICE

[76] Inventor: Robert E. Schubert, 161 F Ave., Coronado, Calif. 92118

[21] Appl. No.: 786,147

[22] Filed: Apr. 11, 1977

[51] Int. Cl.² ............................................. A61C 7/04
[52] U.S. Cl. ...................................................... 32/33
[58] Field of Search ............................... 32/33; 128/20

[56] References Cited

U.S. PATENT DOCUMENTS

| 1,053,965 | 2/1913 | Barghausen et al. | 32/33 |
| 1,155,342 | 10/1915 | DeWitt | 32/33 |
| 2,701,916 | 2/1955 | Jarboe | 32/33 |
| 2,823,455 | 2/1958 | Sprague | 32/33 |
| 2,873,528 | 2/1959 | Thompson | 32/33 |
| 3,456,348 | 7/1969 | Van Lanigan | 32/33 |
| 3,802,081 | 4/1974 | Rogers | 32/33 |
| 3,924,333 | 12/1975 | Erickson | 32/33 |
| 4,024,642 | 5/1977 | Zorovich | 32/33 |

Primary Examiner—Louis G. Mancene
Assistant Examiner—John J. Wilson
Attorney, Agent, or Firm—Brown & Martin

[57] ABSTRACT

A combination mouth prop and oral evacuation device for use by a dentist includes a mouth prop for fitting between the upper and lower jaws for holding the mouth open, an attached, generally U-shaped suction tube secured to the mouth prop and fitted inside the lower jaw below the tongue and inside the teeth, for drawing fluids from within the mouth during dental work therein, and a tongue guard on the suction tube.

5 Claims, 5 Drawing Figures

U.S. Patent  Sep. 18, 1979  4,167,814
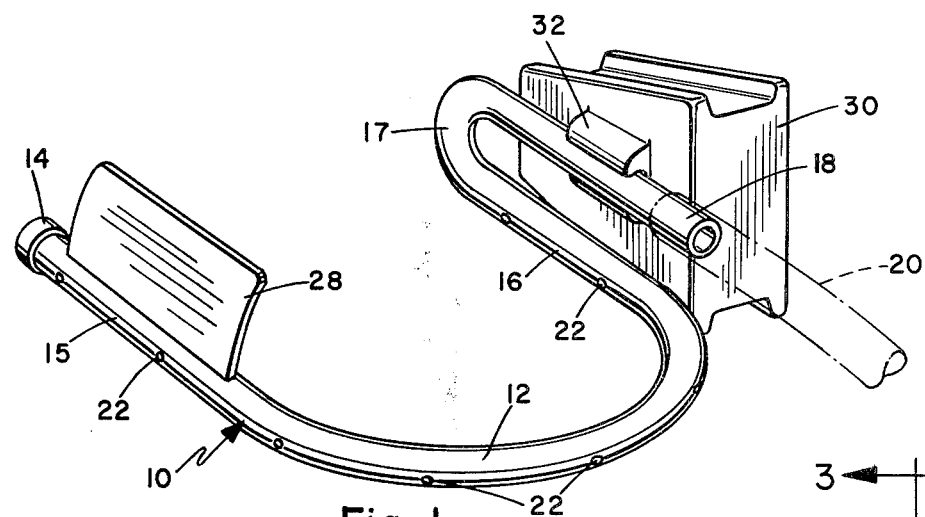
Fig. 1
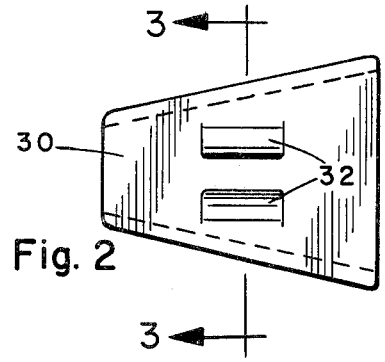
Fig. 2
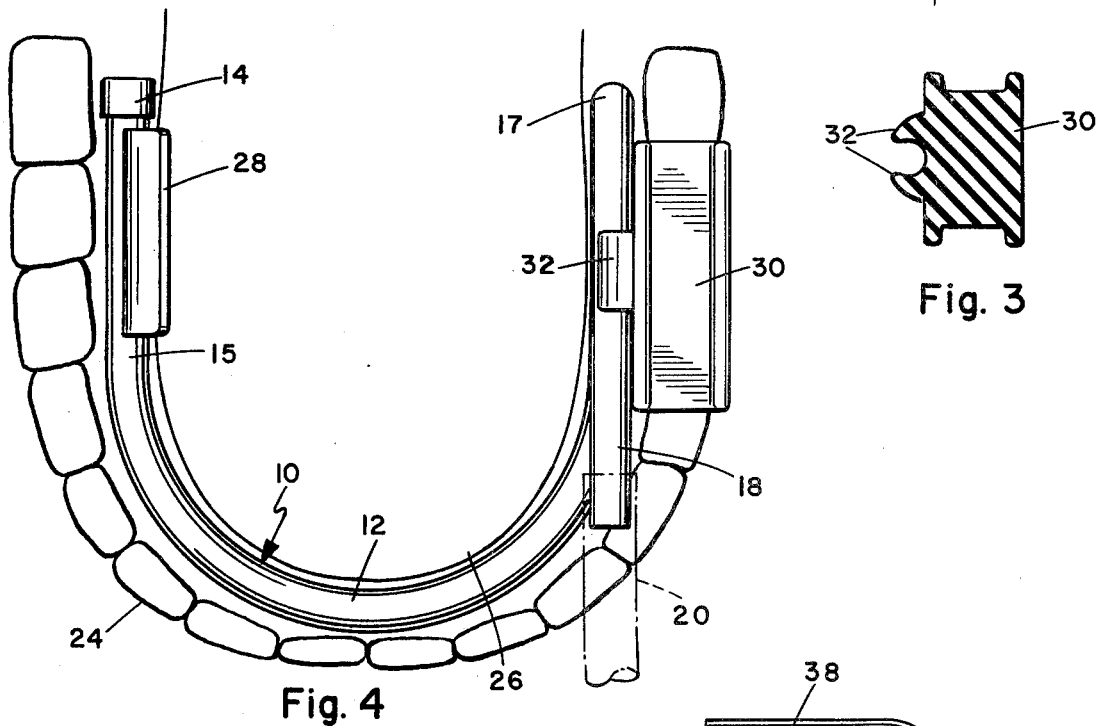
Fig. 3
Fig. 4
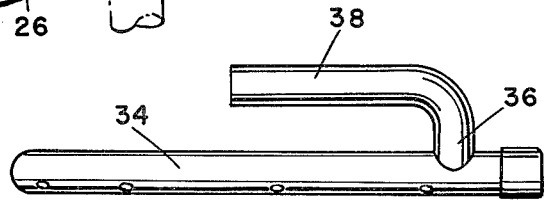
Fig. 5

MOUTH PROP AND ORAL EVACUATION DEVICE

BACKGROUND OF THE INVENTION

The present invention relates to dental apparatus and pertains particularly to a combination oral evacuation device and mouth prop.

During dental work such as the drilling and grinding of teeth a cooling fluid, such as water, is typically sprayed onto the area being drilled or ground for cooling purposes. The fluid also serves as a washing fluid for washing away particles produced by the drilling or grinding process.

It is necessary to constantly remove this fluid during this process. It is also desirable during this time that the mouth be held open and the tongue be held away from the area of work. Numerous mouth evacuation devices and tongue shields have been proposed in the past. However, these have numerous drawbacks and efforts to combine the two have met with very limited success.

One problem with such previous devices is that no adequate means for holding the evacuation device in place has been found. Another problem is that such devices have been complicated and difficult to use.

For this reason the current practice is the use of a hook like evacuation tube which hooks over the teeth of the lower jaw, with the end extending into the lower mouth for evacuation of fluids therefrom. Such device has only a limited intake area and can become quite uncomfortable. It is also necessary during such procedures for the patient to hold the mouth open for work by the dentist. It is also necessary for the dentist or his assistant to hold the tongue to the side with a tongue depressor or the like during the grinding and drilling operation.

Accordingly, it is desirable that some means be available which is easy and convenient to use for the purpose of oral evacualtion, tongue shielding and holding the jaws open.

SUMMARY AND OBJECTS OF THE INVENTION

It is accordingly the primary object of the present invention to overcome the above problems of the prior art.

Another object of the present invention is to provide a combined oral evacuation and mouth prop device.

A further object of the present invention is to provide an oral evacuation device, combined with a mouth prop, that also includes a tongue shield.

In accordance with the primary aspect of the present invention, a generally U-shaped suction tube is fitted within the lower jaw and connected to a generally wedge shaped mouth prop, such that the oral evacuation device is held in place by the mouth prop during use.

The above and other objects and advantages of the present invention will become apparent from the following description when read in conjunction with the drawings, wherein:

FIG. 1 is a perspective view of an oral evacuation and mouth prop device in accordance with the invention.

FIG. 2 is a side elevation view of the mouth prop.

FIG. 3 is a sectional view taken on line 3—3 of FIG. 2.

FIG. 4 is a top plan view of the device of FIG. 1 shown in use.

FIG. 5 is a side elevation view of an alternate vacuum attachment tube arrangement.

DESCRIPTION OF A PREFERRED EMBODIMENT

Turning now to the drawings, particularly to FIG. 1, there is illustrated an oral evacuation and mouth prop device designated generally by the numeral 10, comprising a generally U-shaped suction tube 12 having a closed end 14 at the terminus of one leg 15 of the U. The other leg 16 has an upwardly turned portion 16 with a forwardly extending connecting tube 18, for connecting to a suction hose 20 of a evacuator device. The tube 12 includes a plurality of fluid collecting perforations 22 communicating with the interior of the tube in the generally lower portion thereof. The placement of the perforations in the lower portion of the tube insures that the openings will be underneath the fluid in the mouth and will not lose suction by becoming uncovered.

The tube fits, as best seen in FIG. 4, within the lower jaw inside the row of teeth 24 and below the tongue 26.

A tongue guard 28 is connected in a suitable manner to one leg of the tube 12, for shielding the tongue from a drill and other work implements while working on the teeth. The guard 28 extends upward from the upper portion of the tube 12 and curves slightly inward above the tongue. This puts or keeps the tongue out of the way and provides sufficient room between the guard and the teeth for work thereon. The guard 28 may be attached in substantially any position around the tube 12 as desired. The preferred construction is that the guard 28 be on the opposite leg of the U-shaped tube from the outlet and from the mouth prop.

A mouth prop 30 is secured to the suction tube 12 for holding the tube in place during operation. In a preferred embodiment, shown in FIGS. 2 and 3, the mouth prop 30 is of a generally wedge shaped configuration for fitting between the upper and lower teeth between the upper and lower jaws. The mouth prop 30 is preferably formed of a somewhat resilient plastic or rubber material to avoid damage to the teeth, the basic configuration being well known. The mouth prop and suction tube 12 are preferably secured together by easily releasable means such as resilient detent ribs 32, which may be integral with or attached to the prop. This permits the prop and tube to be constructed independently and of different sizes and selectively assembled by the dentist to fit the mouth of the particular patient. Thus, if a patient has a wide jaw with the ability to open it only a small amount, a small prop would be necessary in combination with a larger U-shaped suction tube. This construction also permits either one or both of the mouth prop and the evacuation tube to be selectively disposable. Thus if the tube 12 were constructed of a easily cleanable material, such as stainless steel so that it could be re-used, while the mouth prop could be constructed of a disposable plastic material. On the other hand, both mouth prop and suction tube may be constructed of a disposable material such as a plastic or the like.

Turning now to FIG. 5 of the drawing, an alternate embodiment is shown. In this embodiment, a U-shaped suction tube 34 is closed at both ends and includes an upwardly extending connecting conduit 36 extending upward from one leg, spaced from the closed end thereof. The connecting conduit has a forwardly extending arm 38 for connection to an existing evacuation or vacuum system. This permits the connecting end of the leg of the U-tube to extend further back in the mouth of the patient.

It will be appreciated that the tubes as specifically illustrated are for working on one side of the mouth. A tube for the opposite side of the mouth would be a mirror image of the above tube, having the vacuum connecting means and the tongue guard on opposite legs of the U-shaped tube. It will be appreciated that other forms of connecting means for connecting the tube to the mouth prop and for connecting the evacuating tube could be used. Such an arrangement could be such that the mouth prop could be connected on either leg of the U-shaped tube, and the tongue guard could also be connected on either leg. With such an arrangement, the vacuum connecting means would similarly be connected to the interior of the tube at a position away from the two legs to permit working without interference therefrom.

While the present invention has been illustrated and described by means of specific embodiments, it is to be understood that numerous changes and modifications may be made therein without departing from the spirit and scope of the invention as defined in the appended claims.

Having described my invention, I now claim:

1. A combination of mouth prop and evacuation device comprising:
    a substantially rigid U-shaped suction tube adapted for fitting in the mouth inside the lower jaw for removing fluids from the mouth, said tube having opposed legs and including a plurality of openings along the length thereof in the lower portion thereof;
    a mouth prop detachably secured to one leg of said suction tube for fitting between the teeth between the upper and lower jaw for holding the mouth open and for holding said suction tube in place wherein said tube lies in the mouth beneath the tongue said mouth prop includes releasable clamp means for clamping to said tube; connecting means on said tube for attachment of a vacuum line adjacent said mouth prop; and
    a tongue guard secured to said suction tube and extending upward therefrom, for separating the tongue from some of the teeth on the lower jaw.

2. The device of claim 1, wherein said suction tube is closed at one end, and the other end is open and curved upward and toward the front for connection to a vacuum line.

3. The device of claim 2, wherein both ends of said tube are closed and said connecting means extends upward from one leg and toward the front.

4. The device of claim 1, wherein said tongue guard is attached to said tube on the leg opposite the mouth prop.

5. The device of claim 1, wherein said mouth prop is substantially wedge shaped.